US009717528B2

(12) United States Patent
Singh

(10) Patent No.: US 9,717,528 B2
(45) Date of Patent: Aug. 1, 2017

(54) EXTERNAL FIXATOR WITH Y STRUT

(71) Applicant: Stryker European Holdings I, LLC, Kalamazoo, MI (US)

(72) Inventor: Manoj Kumar Singh, Mahwah, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 111 days.

(21) Appl. No.: 14/669,157

(22) Filed: Mar. 26, 2015

(65) Prior Publication Data

US 2015/0272624 A1 Oct. 1, 2015

Related U.S. Application Data

(60) Provisional application No. 61/973,349, filed on Apr. 1, 2014.

(51) Int. Cl.
*A61B 17/66* (2006.01)
*A61B 17/62* (2006.01)

(52) U.S. Cl.
CPC .................... *A61B 17/62* (2013.01)

(58) Field of Classification Search
CPC ............. A61B 2017/567; A61B 17/60; A61B 2017/603; A61B 17/62; A61B 17/64; A61B 17/6416; A61B 17/6425; A61B 17/6433; A61B 17/6441; A61B 17/645; A61B 17/6458; A61B 17/6466; A61B 17/6475; A61B 17/6483; A61B 17/6491; A61B 17/66

See application file for complete search history.

(56) References Cited

U.S. PATENT DOCUMENTS

| 2,055,024 | A | * | 9/1936 | Bittner, Jr. | ............. | A61B 17/62 606/56 |
| 4,338,927 | A | | 7/1982 | Volkov et al. | | |
| 5,681,309 | A | * | 10/1997 | Ross, Jr. | ................ | A61B 17/62 606/54 |
| 5,702,389 | A | | 12/1997 | Taylor et al. | | |
| 5,971,984 | A | | 10/1999 | Taylor et al. | | |
| 6,129,727 | A | * | 10/2000 | Austin | ................... | A61B 17/62 606/56 |
| 7,226,449 | B2 | | 6/2007 | Venturini et al. | | |
| 7,708,736 | B2 | | 5/2010 | Mullaney | | |
| 7,955,334 | B2 | | 6/2011 | Steiner et al. | | |

(Continued)

*Primary Examiner* — Lynnsy Summitt
(74) *Attorney, Agent, or Firm* — Lerner, David, Littenberg, Krumholz & Mentlik, LLP

(57) ABSTRACT

An external fixation system includes top and bottom fixation plates that may be connected to fragments of a bone. At least one y-shaped strut attaches the two fixation plates. Each y-shaped strut has first, second and third telescopic struts coupled at a connector joint. The first strut member is coupled to the top fixation plate and the second and third strut members are coupled to the bottom fixation plate. Each strut member may include a joint and may also include an actuation unit connecting the particular strut member to the top or bottom fixation plate. Rotation of a head portion of the actuation unit causes rotation of a threaded rod, causing adjustment in the length of the respective strut member. As the lengths of the strut members change, the joints may reposition, leading to the top fixation plate becoming repositioned with respect to the bottom fixation plate.

18 Claims, 3 Drawing Sheets

(56) References Cited

U.S. PATENT DOCUMENTS

| | | | |
|---|---|---|---|
| 8,057,474 B2 | 11/2011 | Knuchel et al. | |
| 8,333,766 B2 * | 12/2012 | Edelhauser | A61B 17/62 606/55 |
| 8,834,467 B2 * | 9/2014 | Singh | 606/56 |
| 8,945,128 B2 * | 2/2015 | Singh | A61B 17/62 606/54 |
| 2003/0149430 A1 | 8/2003 | Ferrante et al. | |
| 2003/0181911 A1 | 9/2003 | Venturini | |
| 2009/0036890 A1 * | 2/2009 | Karidis | A61B 17/62 606/56 |
| 2009/0177198 A1 | 7/2009 | Theodoros et al. | |
| 2011/0313419 A1 | 12/2011 | Mullaney | |
| 2012/0041439 A1 * | 2/2012 | Singh | A61B 17/62 606/54 |
| 2012/0150180 A1 | 6/2012 | Verma et al. | |
| 2014/0058389 A1 | 2/2014 | Singh et al. | |

* cited by examiner

EXTERNAL FIXATOR WITH Y STRUT

CROSS-REFERENCE TO RELATED APPLICATIONS

The present application claims the benefit of the filing date of U.S. Provisional Patent Application No. 61/973,349, filed Apr. 1, 2014, the disclosure of which is hereby incorporated by reference herein.

FIELD OF THE INVENTION

The present invention relates to systems and methods for correcting bone deformities, and in particular it relates to external fixation systems having Y-struts.

BACKGROUND OF THE INVENTION

External fixation frames may be used to correct skeletal deformities. The Ilizarov external fixation devices, for example, are widely used for this purpose. The Ilizarov-type devices may be used to translate bone segments by manipulating rings connected to each bone segment and a plurality of threaded rods connected to the manipulation rings.

A bone fragment can be moved, in general, from its original position as in a nonunion or malunion or from its intended position as in congenital deformities along six separate axes, a combination of three orthogonal translational axes (e.g., typical "X," "Y" and "Z" axes) and three orthogonal rotational axes (e.g., rotation about such typical "X," "Y" and "Z" axes). This movement generally occurs via manipulation of one or more adjustable length struts connected at each end thereof to rings of the external fixation device.

External fixation devices are generally attached to the boney skeleton, such as the femur or tibia, for example, with threaded and/or smooth pins and/or threaded and/or smooth and/or beaded wires. Such constructs are commonly referred to as orthopedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

Examples of external fixation devices include those described in U.S. Pat. No. 8,333,766 and U.S. Patent Publication No. 2014/0058389, the disclosures of which are both hereby incorporated by reference herein. After a bone is fixed to such an external fixation device, one bone fragment may be moved in any combination of the six degrees of freedom relative to a fixed bone fragment. The movement is generally directed by a preoperative and/or postoperative plan defining precise movement of rings and/or struts to result in precise movement of one bone fragment relative to a fixed bone fragment.

BRIEF SUMMARY OF THE INVENTION

The present invention is directed to apparatus and methods for repositioning a first bone fragment with respect to a second bone fragment. In one embodiment, an external fixation system includes top and bottom fixation plates each having upper and lower plate surfaces, and at least one y-shaped strut having first, second, and third strut members coupled at a connector joint. One of the first, second and third strut members is coupled to one of the top and bottom fixation plates and the two of the first, second and third strut members are coupled to the other of the top and bottom fixation plates. An actuation unit may be coupled to an end of at least one of the first, second, and third strut members of the y-shaped strut and either top or bottom fixation plate, the actuation unit for adjusting a length of the at least one of the first, second, and third strut members. The actuation unit may include a housing having a borehole and an outer surface configured to lie adjacent to an inner surface of a hole in either the top or bottom fixation plate when the housing is coupled to either the top or bottom fixation plate. The actuation unit may also include a rotatable head located on a first side of the top or bottom fixation plate to which the actuation unit is coupled, and a portion connected to an end of the at least one of the first, second, and third strut members and located on a second side of the top or bottom fixation plate to which the actuation unit is coupled, the first side being opposite the second side. Actuation of the rotatable head may actuate the portion connected to the end of the at least one of the first, second, and third strut members, causing adjustment in the length of the at least one of the first, second and third strut members. The first, second, and third strut members may each include a threaded rod coupled to a tubular sleeve. A rotatable wheel may be coupled to the threaded rod of at least one of the first, second, and third strut members, rotation of the rotatable wheel configured to rotate the threaded rod. The threaded rod of the first, second, and third strut members may be configured to move axially into or out of the respective tubular sleeve of the first, second, and third strut members. A first end of each threaded rod may be a free end, and a second end of each threaded rod opposite the first end may be coupled to a joint, such as a universal joint.

According to another embodiment of the disclosure, an external fixation system includes top and bottom fixation plates each having upper and lower plate surfaces, and at least one y-shaped strut having first, second, and third plate connections. One of the first, second, and third plate connections is directly coupled to one of the top or bottom fixation plates and the other two of the first, second, and third plate connections are directly coupled to the other of the top or bottom fixation plates. The at least one y-shaped strut may have first, second, and third strut members coupled at a connector joint. The connector joint may include first and second joints selected from the group consisting of fixed joints, ball joints, and universal joints. An actuation unit may be coupled to an end of at least one of the first, second, and third strut members of the y-shaped strut and either top or bottom fixation plate, the actuation unit for adjusting a length of the at least one of the first, second, and third strut members. The actuation unit may include a housing having a borehole and an outer surface configured to lie adjacent to an inner surface of a hole in either the top or bottom fixation plate when the housing is coupled to either the top or bottom fixation plate. The actuation unit may also include a rotatable head located on a first side of the top or bottom fixation plate to which the actuation unit is coupled, and a portion connected to an end of the at least one of the first, second, and third strut members and located on a second side of the top or bottom fixation plate to which the actuation unit is coupled, the first side being opposite the second side. Actuation of the rotatable head may actuate the portion connected to the end of the at least one of the first, second, and third strut members, causing adjustment in the length of the at least one of the first, second and third strut members. The first, second, and third strut members may each include a threaded rod coupled to a tubular sleeve, and a first end of each threaded rod may be a free end, and a second end of each threaded rod opposite the first end may be coupled to a joint. A rotatable wheel may be coupled to the threaded rod of at least one of the first, second, and third strut members, rotation of the rotatable wheel configured to rotate the threaded rod. The threaded rod of the first strut member may define a first longitudinal axis, the threaded rod of the second strut member may define a second longitudinal axis, and the threaded rod of the third strut member may define a third longitudinal axis. A first angle defined between the first and second longitudinal axes may be between about 20 degrees and about 70 degrees, and a second angle defined between the second and third longitudinal axes may be between about 20 degrees and about 70 degrees.

According to still another embodiment of the disclosure, an external fixation system includes top and bottom fixation plates, and at least one y-shaped strut having first, second, and third plate connections and first, second and third strut portions. One of the first, second, and third plate connections is directly coupled to one of the top or bottom fixation plates and the other two of the first, second, and third plate connections are directly coupled to the other of the top or bottom fixation plates. The first, second and third strut portions are coupled at a connector joint.

DETAILED DESCRIPTION

As used herein, the term "distal" means more distant from the heart and the term "proximal" means closer to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body. When used in relation to an external fixation device, these terms are used as if device is attached to a leg of a patient in an intended manner.

Figure 1:
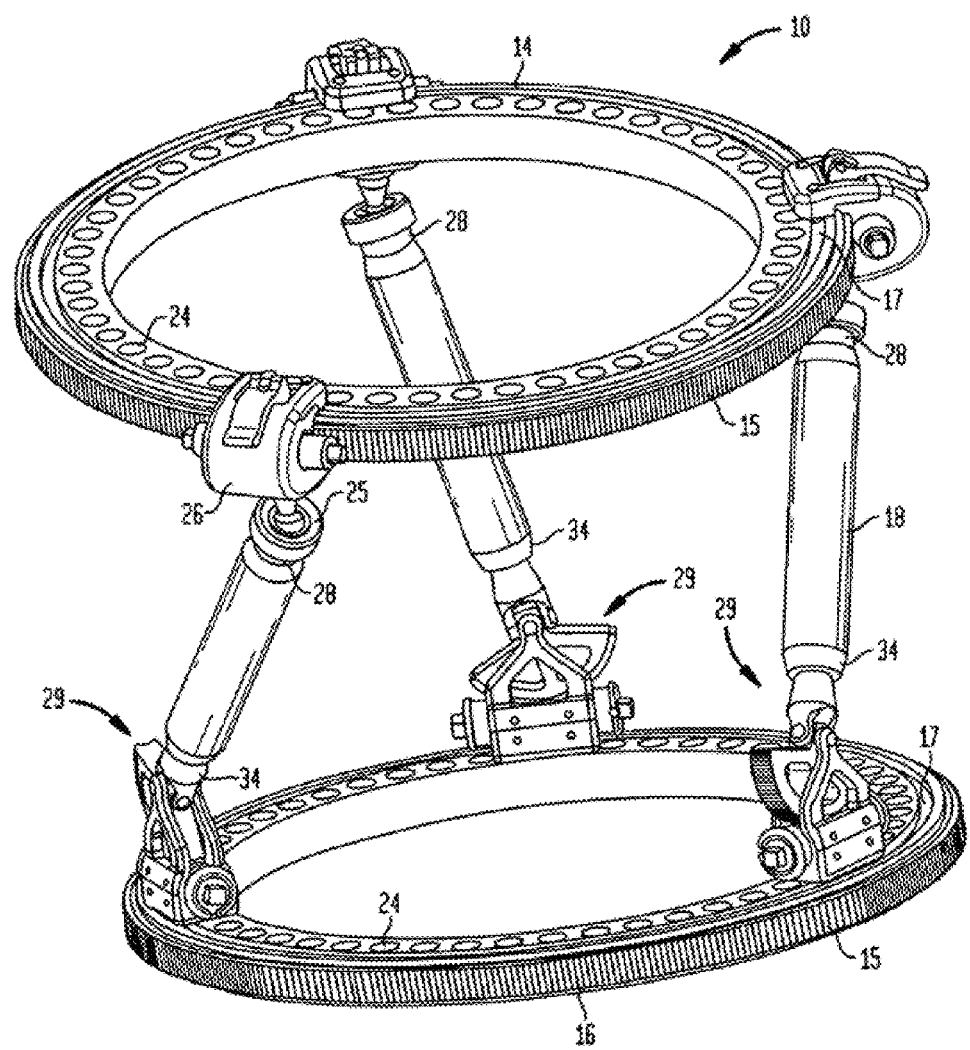
FIG. 1 is a perspective view of an external fixation device according to the prior art.

Referring to FIG. 1, there is shown an external fixation system 10 for correcting a bone deformity according to the prior art. The external fixation system 10 may be utilized with any long bone, in particular, the tibia and the femur.

As shown in FIG. 1, the external fixation system 10 includes a first ring 14 and a second ring 16. In some embodiments, both rings 14, 16 are identical. Each ring 14 includes a worm gear 15 formed around its outer circumference. Two grooves 17 are formed in the upper and lower surfaces of ring 14 around its circumference adjacent the worm gear 15. Ring 14 (or 16) may include a multi level configuration with the upper and lower surfaces having alternate steps including through holes 24. Such an external fixation ring (without the circumferential worm gear) is described in U.S. Pat. No. 7,955,334, the disclosure of which is hereby incorporated by reference herein. In certain embodiments, rings 14, 16 are connected by three variable length struts 18. The three struts 18 have first ends 28 mounted to the first ring 14 via a connector 25 coupled to a sliding or shuttle unit 26, which is circumferentially moveable around ring 14. In several embodiments, the first ends 28 are connected to sliding units or connector 26 by a connector 25 having a ball or spherical joint. As is typical, the rings are connected to a tibia (not illustrated in FIG. 1) by a plurality of bone pins or wires (not shown). In some embodiments, the pins or wires are connected to each ring 14, 16 by connection elements, which are located in one or more of a multiplicity of holes 24 around the circumference of the first and second rings 14 and 16. Although holes 24 are shown, any structure which locates the pins or wires with respect to the circumference of rings 14 and 16 can be utilized. Lower ends 34 of struts 18 may be connected to lower ring 16 by standard universal-joints, which allow free rotation about only two axes rather than the three axes of the spherical joint at the first strut end 28.

Ring 14 may be coupled to a first bone element via pins or wires and, similarly, ring 16 is coupled to a second bone element by similar pins or wires. Shuttle unit 26 is slidable about ring 14 in a track and is preferably driven by a servo motor. A second connector 29 between strut 18 and second lower ring 16 has a standard universal joint, which allows the strut to rotate freely about two axes oriented perpendicular with respect to the one another. The universal joint may also be powered by servo motors. Thus, each of the three sliding shuttle units 26 may be independently controlled and the three connectors 29 at the second ring 16 may be independently controlled so that the ring 14, and therefore the bone element attached to ring 14, can be positioned in proper alignment with ring 16 and the bone element attached to ring 16. Rings 14 and 16 can be repositioned after their initial alignment as desired by the surgeon. In addition, the movement can be programmed into a computer means, which can automatically increment movement, for example, on a daily basis. Strut 18 is of variable length but can be locked at a desired length after the surgeon initially sets the starting location of the system.

Figure 2:
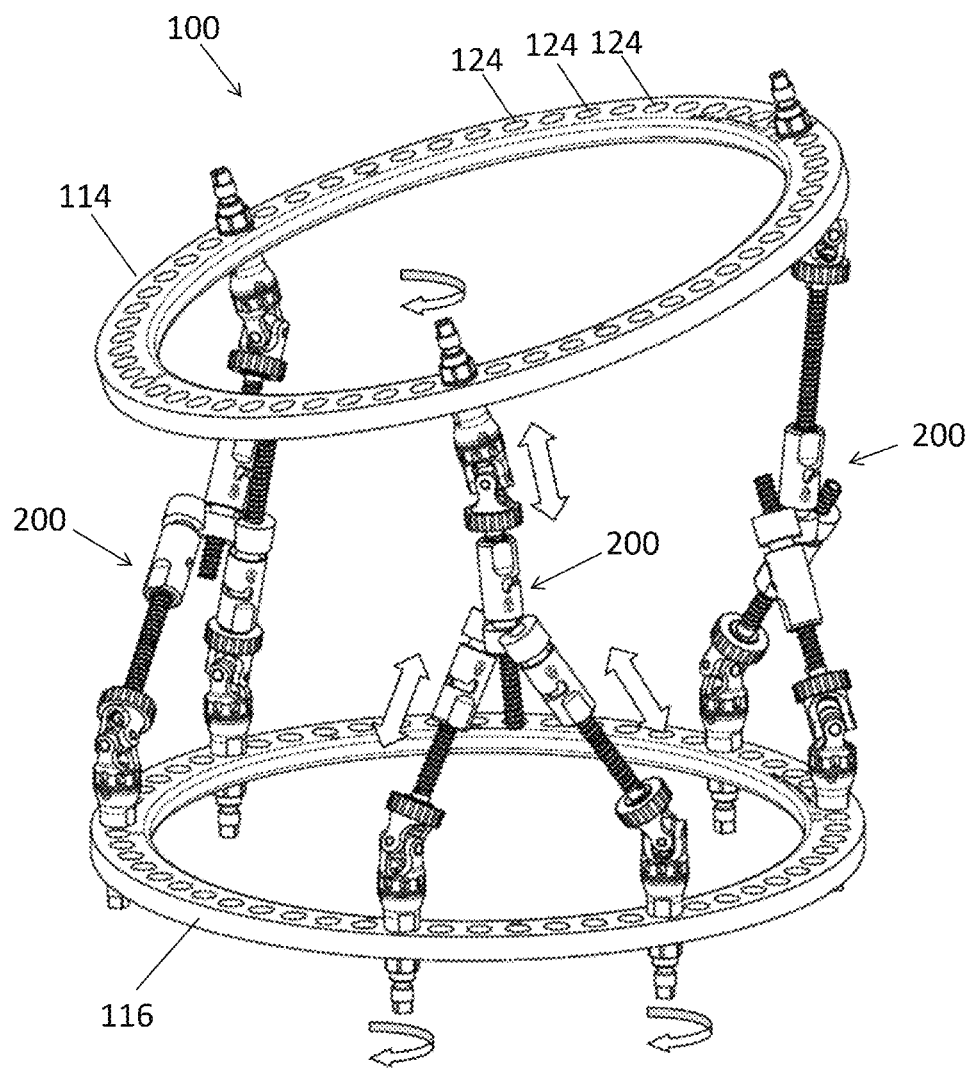
FIG. 2 is a perspective view of an external fixation device according to the present invention.

Referring to FIG. 2, there is shown an external fixation system 100 according to an aspect of the invention. Generally, the external fixation system 100 includes a first support member, such as a first ring 114, and a second support member, such as a second ring 116. The first ring 114 may be attached to a first bone fragment, such as a proximal portion of a tibia (not illustrated), and the second ring 116 may be attached to a second bone fragment, such as a distal portion of a tibia (not illustrated). The first and second ring 114, 116 may be attached to the first and second bone fragments by conventional means, including wires and/or pins (not illustrated). It should also be understood that, although support members 114, 116 take the form of rings in FIG. 2, other support members, including other plate type supports besides rings, may be suitable for use in the present invention, such as half rings or u-shaped rings, for example.

First ring 114 is connected to second ring 116 by a plurality of adjustable-length struts. The first and second rings 116 may each have a plurality of through-holes 124 extending from a top surface of the rings to a bottom surface of the rings. The adjustable-length struts may be attached to the rings 114, 116, through the through-holes 124. In the illustrated embodiment, three struts connect first ring 114 to second ring 116, each strut taking the form of a Y-strut 200. Each Y-strut 200 includes three telescopic components, the lengths of which may be independently adjusted to gradually reposition first ring 114 with respect to second ring 116 (and thus the first bone fragment in relation to the second bone fragment) with six degrees of freedom.

Figure 3:
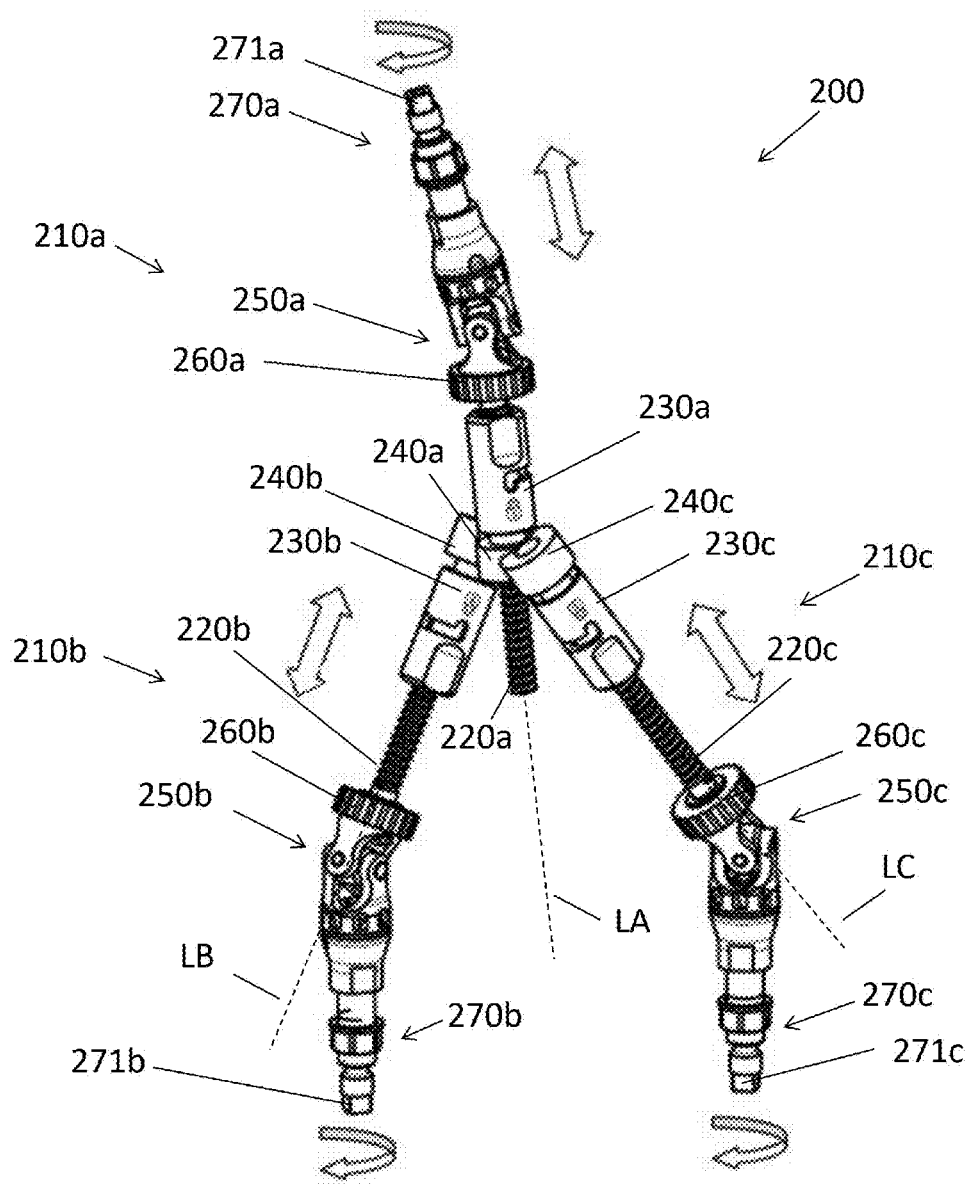
FIG. 3 is a perspective view of a Y-strut of the external fixation device of FIG. 2.

Y-strut 200 is illustrated in greater detail in FIG. 3. Generally, Y-strut 200 includes three similar or identical telescopic struts 210*a-c* coupled together in a Y-shape. The telescopic struts 210*a-c* include threaded rods 220*a-c* at least partially located within bores of tubular sleeves 230*a-c*, respectively. As illustrated by the double-sided arrows in FIGS. 2-3, the threaded rods 220*a-c* may axially translate in opposing directions with respect to the tubular sleeves 230*a-c*. The tubular sleeves 230*a-c* may each at least partially comprise a quick-release mechanism as is described in U.S. Pat. No. 8,057,474, the disclosure of which is hereby incorporated by reference herein. Briefly, the tubular sleeves 230*a-c* may be rotated from a first unlocked position in which the threaded rods 220*a-c* may freely axially translate with respect to the tubular sleeves into a second locked position in which the threaded rods may only axially translate with respect to the tubular sleeves upon rotation of the threaded rods 220*a-c*. This may be achieved, at least in part, by the tubular sleeves 230*a-c* having an elliptical bore, such that, in the first unlocked position, there is clearance between bearing members (not illustrated) inside the tubular sleeves and the threads of the threaded rods 220*a-c*. When rotated to the second locked position, the oblong bore is also rotated, forcing the bearing members into contact between successive threads of the threaded rods 220*a-c*, such that the rods may only axially translate upon rotation. In one embodiment, a connector 240*a* is located at a distal end of telescopic strut 210*a*, or, stated another way, at an end of the telescopic strut remote from the fixation ring (first ring 114) to which the telescopic strut is connected. On the other hand, connectors 240*b-c* are located at proximal ends of telescopic struts 210*b-c*, respectively. Stated another way, connectors 240*b-c* are located at ends of the telescopic struts 210*b-c*, respectively, remote from the fixation ring (second ring 116) to which the telescopic struts are connected. Connectors 240*a-c* may be fixed with respect to one another. Alternatively, connectors 240*a-c* maybe movable with respect to one another. For example, adjacent connectors 240*a* and 240*b* may be coupled by a pin to provide rotation about a single axis, by a ball joint to provide for polyaxial movement, or by a universal joint to provide three degrees of rotation about a coincident point. Connectors 240*a* and 240*c* may be coupled in an identical manner to connectors 240*a* and 240*b*.

Each threaded rod 220*a-c* may have a first free end and second end remote form the first end. As illustrated in FIG. 3, the free end of threaded rod 220*a* is the distal end, while the free ends of threaded rods 220*b-c* are the proximal ends. The second ends of the threaded rods 220*a-c* may be coupled to a first portion of a joint. The joints may take the form of universal joints 250*a-c*. Generally, the universal joints 250*a-c* may include a first joint portion pivotably connected to a second joint portion, the first and second joint portions being capable of rotating about three orthogonal axes. The first joint portion of each universal joint 250*a-c* may be coupled to the second end of the respective threaded rod 220*a-c*, while the second joint portion may be coupled to an actuation unit 270*a-c*, described in greater detail below. The first joint portion of each universal joint 250*a-c* may include a generally circular wheel 260*a-c*, respectively. The wheels 260*a-c* may be fixed to the first joint portions of the universal joints 250*a-c* such that rotation of the wheel causes rotation of the respective threaded rods 220*a-c* and first joint portions. As described in greater detail below, this may allow a user to adjust the length of the threaded rods by hand by turning the desired wheel 260*a-c*. Threaded rods 220*a*, 220*b*, and 220*c* may each extend along longitudinal axes LA, LE, and LC, respectively. The angle formed between axes LA and LB may between about 10 degrees and about 80 degrees, between about 20 degrees and about 70 degrees, or between about 30 degrees and about 60 degrees. Similarly, the angle formed between axes LA and LC may between about 10 degrees and about 80 degrees, between about 20 degrees and about 70 degrees, or between about 30 degrees and about 60 degrees.

The actuation units 270*a-c*, which may also be referred to as top-click mechanisms or motor-click mechanisms, may include housings having a borehole and outer surfaces that serve as plate connection portions. For example, the actuation units 270*a-c* may include cylindrical portions configured to be inserted through, and lie adjacent to, the circular through-holes 124 of the first and second rings 114, 116. The actuation units 270*a-c* may also include rotatable square heads 271*a-c* to provide an interface to mate with a screw driver or other tool. Although illustrated as squares, other shapes may be acceptable. The square heads 271*a-c* may be located on a first side of the particular ring to which the actuation units is attached. The actuation units 270*a-c* may also include portions connected to an end of a respective telescopic strut 210*a-c*, located on a second side of the particular ring to which the actuation unit is attached, the second side being opposite the first side. Rotation of a particular square head 271*a-c* causes the respective universal joint 250*a-c* to rotate in unison, causing, in turn, the respective threaded rod 220*a-c* to rotate. With the quick-release mechanism in the locked position, rotation of a particular square head 271*a-c* causes the respective threaded rod 220*a-c* to rotate with respect to the quick-release mechanism, and thus axially translate into or out of the bore of the quick release mechanism, adjusting the length of the particular telescopic strut 210*a-c*. The actuation units 270*a-c* may be equipped with internal ball and spring mechanisms (not shown) such that friction must be overcome to rotate the square heads 271*a-c*. As the square heads 271*a-c* are rotated, balls may sequentially mate with corresponding grooves. Each time a ball enters a sequential groove, the actuation units 270*a-c* may provide tactile and/or audible feedback in the form of "clicks," with each "click" corresponding to a medically relevant distance of axial translation of the threaded rods 220*a-c*. Suitable actuation units are described in more detail in U.S. Pat. Nos. 8,834,467 and 8,945,128, the disclosures of which are both hereby incorporated by reference herein.

In use, a Y-strut 200 may be connected to first and second rings 114, 116. A connecting portion of actuation unit 270*a* may be passed through a through-hole 124 of first ring 114, and connection portions of actuation units 270*b-c* may each be passed through a through-hole 124 of second ring 116. This may be repeated two times such that three Y-struts 200 connect first ring 114 to second ring 116. With each quick-release mechanism in the unlocked position, the length of each telescopic strut 210*a-c* of each Y-strut 200 may be quickly adjusted to a desired length. Once at the desired length, the quick-release mechanism may be rotated to the locked position such that additional axial movement of the threaded rods 220*a-c* through the tubular sleeves 230*a-c* may occur only by rotation of the threaded rods with respect to the tubular sleeves. When the entire fixation system 100 is in the desired configuration, first ring 114 may be coupled to a first bone portion, such as a proximal tibia, and second ring 116 may be coupled to a second bone portion, such as a distal tibia. The surgeon or other personnel may create a correction plan, using for example a computer program, that indicates how often each actuation unit 270*a-c* of each Y-strut 200 should be rotated (or "clicked") such that the gradual increase or decrease in lengths of the telescopic struts 210*a-c* causes the gradual repositioning of first and second rings 114, 116, and thus first and second bone fragments, relative to one another.

As the telescopic struts 210*a-c* of each Y-strut 200 change length, the universal joints 250*a-c* reposition, causing first ring 114 to change position with respect to second ring 116, until the attached bone fragments have been repositioned as desired. Each rotation or "click" of each actuation mechanism 270*a-c* may be performed using a tool that interfaces with the square heads 271*a-c* of the actuation units. This tool may be a "smart" tool and automatically actuate the actuation units 270*a-c* according to the correction plan. Such a smart tool is described in greater detail in U.S. Patent Publication No. 2012/0150180, the entire contents of which are hereby incorporated by reference herein. However, if desired, a user, including the patient, may manually rotate the wheel 260*a-c* of a given telescopic strut 210*a-c* to increase or decrease the length of the respective telescopic strut.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. In addition, although general being described for use with the tibia, the external fixation devices described herein may be used along with any long bone in the body.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An external fixation system comprising:
   top and bottom fixation plates each having upper and lower plate surfaces; and
   at least one y-shaped strut having first, second, and third telescopic adjustable-length strut members coupled at a connector joint,
   wherein one of the first, second and third strut members is coupled to one of the top and bottom fixation plates and the other two of the first, second and third strut members are coupled to the other of the top and bottom fixation plates;
   wherein the first, second, and third strut members each include a threaded rod coupled to a tubular sleeve,
   wherein each strut member is coupled to the top fixation plate or the bottom fixation plate by a plate joint such that each strut member is pivotable about the plate joint and with respect to the corresponding fixation plate to which each strut member is coupled.

2. The external fixation system of claim 1 further comprising:
   an actuation unit coupled to an end of at least one of the first, second, and third strut members of the y-shaped strut and either top or bottom fixation plate, the actuation unit for adjusting a length of the at least one of the first, second, and third strut members.

3. The external fixation system of claim 2, wherein the actuation unit further comprises:
   a housing having a borehole and an outer surface configured to lie adjacent to an inner surface of a hole in either the top or bottom fixation plate when the housing is coupled to either the top or bottom fixation plate.

4. The external fixation system of claim 3, wherein the actuation unit further comprises:
   a rotatable head located on a first side of the top or bottom fixation plate to which the actuation unit is coupled; and
   a portion connected to an end of the at least one of the first, second, and third strut members and located on a second side of the top or bottom fixation plate to which the actuation unit is coupled, the first side being opposite the second side.

5. The external fixation system of claim 4, wherein actuation of the rotatable head actuates the portion connected to the end of the at least one of the first, second, and third strut members, causing adjustment in the length of the at least one of the first, second and third strut members.

6. The external fixation system of claim 1, further comprising a rotatable wheel coupled to the threaded rod of at least one of the first, second, and third strut members, rotation of the rotatable wheel configured to rotate the threaded rod.

7. The external fixation system of claim 1, wherein the threaded rod of the first, second, and third strut members is configured to move axially into or out of the respective tubular sleeve of the first, second, and third strut members.

8. The external fixation system of claim 1, wherein a first end of each threaded rod is a free end, and a second end of each threaded rod opposite the first end is coupled to the plate joint.

9. The external fixation system of claim 8, wherein the plate joint is a universal joint.

10. An external fixation system comprising:
    top and bottom fixation plates each having upper and lower plate surfaces; and
    at least one y-shaped strut having first, second, and third plate connections and having first, second, and third telescopic adjustable-length struts,
    wherein one of the first, second, and third plate connections is directly coupled to one of the top or bottom fixation plates and the other two of the first, second, and third plate connections are directly coupled to the other of the top or bottom fixation plates,
    wherein the first, second, and third adjustable-length struts each include a threaded rod coupled to a tubular sleeve,
    wherein each adjustable-length strut is coupled to the top fixation plate or the bottom fixation plate by a plate joint such that each adjustable-length strut is pivotable about the plate joint and with respect to the corresponding fixation plate to which each adjustable-length strut is coupled.

11. The external fixation system of claim 10, wherein the first, second, and third adjustable-length struts are coupled at a connector joint.

12. The external fixation system of claim 11, wherein the connector joint includes first and second connector joints selected from the group consisting of fixed joints, ball joints, and universal joints.

13. The external fixation system of claim 11, further comprising:
    an actuation unit coupled to an end of at least one of the first, second, and third strut adjustable-length struts of the y-shaped strut and either top or bottom fixation plate, the actuation unit for adjusting a length of the at least one of the first, second, and third adjustable-length struts.

14. The external fixation system of claim 13, wherein the actuation unit further comprises:
a housing having a borehole and an outer surface configured to lie adjacent to an inner surface of a hole in either the top or bottom fixation plate when the housing is coupled to either the top or bottom fixation plate.

15. The external fixation system of claim 14, wherein the actuation unit further comprises:
a rotatable head located on a first side of the top or bottom fixation plate to which the actuation unit is coupled; and
a portion connected to an end of the at least one of the first, second, and third adjustable-length struts and located on a second side of the top or bottom fixation plate to which the actuation unit is coupled, the first side being opposite the second side,
wherein actuation of the rotatable head actuates the portion connected to the end of the at least one of the first, second, and third adjustable-length struts, causing adjustment in the length of the at least one of the first, second and third adjustable-length struts.

16. The external fixation system of claim 11, wherein a first end of each threaded rod is a free end, and a second end of each threaded rod opposite the first end is coupled to the plate joint.

17. The external fixation system of claim 16, further comprising a rotatable wheel coupled to the threaded rod of at least one of the first, second, and third adjustable-length struts, rotation of the rotatable wheel configured to rotate the threaded rod.

18. The external fixation system of claim 16, wherein the threaded rod of the first adjustable-length strut defines a first longitudinal axis, the threaded rod of the second adjustable-length strut defines a second longitudinal axis, and the threaded rod of the third adjustable-length strut defines a third longitudinal axis, a first angle defined between the first and second longitudinal axes being between about 20 degrees and about 70 degrees, and a second angle defined between the second and third longitudinal axes being between about 20 degrees and about 70 degrees.

* * * * *